(12) United States Patent
Kerkhoffs et al.

(10) Patent No.: US 12,017,058 B2
(45) Date of Patent: Jun. 25, 2024

(54) INTRAVASCULAR BLOOD PUMP WITH CERAMIC INNER SLEEVE

(71) Applicant: Abiomed Europe Gmbh, Aachen (DE)

(72) Inventors: Wolfgang Kerkhoffs, Aachen (DE); Thorsten Siess, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 150 days.

(21) Appl. No.: 16/981,544

(22) PCT Filed: Mar. 20, 2019

(86) PCT No.: PCT/EP2019/057011
§ 371 (c)(1),
(2) Date: Sep. 16, 2020

(87) PCT Pub. No.: WO2019/180104
PCT Pub. Date: Sep. 26, 2019

(65) Prior Publication Data
US 2021/0015982 A1 Jan. 21, 2021

(30) Foreign Application Priority Data
Mar. 23, 2018 (EP) ..................................... 18163761

(51) Int. Cl.
*A61M 60/829* (2021.01)
*A61M 60/13* (2021.01)
(Continued)

(52) U.S. Cl.
CPC .......... *A61M 60/829* (2021.01); *A61M 60/13* (2021.01); *A61M 60/174* (2021.01);
(Continued)

(58) Field of Classification Search
CPC .......... A61M 33/02; A61M 2205/0211; A61M 2207/00; A61M 60/135; A61M 60/148;
(Continued)

(56) References Cited

U.S. PATENT DOCUMENTS 4,846,152 A * 7/1989 Wampler ............... F04D 29/047
600/16
5,049,134 A * 9/1991 Golding .............. F04D 13/0673
417/423.1
(Continued)

FOREIGN PATENT DOCUMENTS

CN 205163763 U 4/2016
JP H0610886 A 1/1994
(Continued)

OTHER PUBLICATIONS

Written Opinion from corresponding Singapore Patent Application No. 11202008482U dated Apr. 1, 2022 (6 pp).
(Continued)

*Primary Examiner* — Sang K Kim
(74) *Attorney, Agent, or Firm* — Botos Churchill IP Law LLP

(57) ABSTRACT

An intravascular blood pump having a pumping device including an impeller and an electric motor for driving the impeller. A rotor of the electric motor is disposed inside a cavity in the pumping device and rotatable about an axis of rotation and coupled to the impeller so as to be able to cause rotation of the impeller. The cavity is formed by an inner sleeve made of a ceramic material. At least a portion of the stator of the electric motor, in particular a coil winding, may be arranged on the ceramic inner sleeve.

20 Claims, 3 Drawing Sheets

(51) Int. Cl.
*A61M 60/174* (2021.01)
*A61M 60/216* (2021.01)
*A61M 60/422* (2021.01)
*A61M 60/81* (2021.01)
*A61M 60/825* (2021.01)
*A61M 60/857* (2021.01)

(52) U.S. Cl.
CPC ........ *A61M 60/216* (2021.01); *A61M 60/422* (2021.01); *A61M 60/81* (2021.01); *A61M 60/825* (2021.01); *A61M 60/857* (2021.01); *A61M 2205/0211* (2013.01); *A61M 2205/0283* (2013.01); *A61M 2207/00* (2013.01)

(58) Field of Classification Search
CPC .............. A61M 60/205; A61M 60/419; A61M 60/422; A61M 60/818; A61M 60/829
See application file for complete search history.

(56) References Cited

U.S. PATENT DOCUMENTS

| | | | | |
|---|---|---|---|---|
| 5,527,159 | A * | 6/1996 | Bozeman, Jr. | F04B 17/03 417/244 |
| 5,957,672 | A * | 9/1999 | Aber | A61M 60/237 417/423.12 |
| 6,058,593 | A * | 5/2000 | Siess | H02K 5/124 310/43 |
| 6,158,984 | A * | 12/2000 | Cao | A61M 60/422 417/423.1 |
| 6,227,820 | B1 * | 5/2001 | Jarvik | F16C 32/0427 417/423.12 |
| 6,302,910 | B1 * | 10/2001 | Yamazaki | A61M 60/17 623/3.13 |
| 6,716,157 | B2 * | 4/2004 | Goldowsky | A61M 60/122 600/16 |
| 7,011,620 | B1 | 3/2006 | Siess | |
| 7,798,952 | B2 * | 9/2010 | Tansley | A61M 60/824 600/16 |
| 8,641,594 | B2 * | 2/2014 | LaRose | A61M 60/824 600/16 |
| 9,550,017 | B2 | 1/2017 | Spanier et al. | |
| 9,968,719 | B2 * | 5/2018 | Colella | A61F 2/848 |
| 2001/0041934 | A1 | 11/2001 | Yamazaki et al. | |
| 2007/0156006 | A1 * | 7/2007 | Smith | A61M 60/216 600/16 |
| 2009/0134734 | A1 * | 5/2009 | Nashiki | B60L 7/00 318/400.27 |
| 2010/0041939 | A1 * | 2/2010 | Siess | F04D 13/064 600/16 |
| 2010/0121438 | A1 | 5/2010 | Jarvik | |
| 2010/0261140 | A1 | 10/2010 | Klee et al. | |
| 2015/0038770 | A1 * | 2/2015 | Colella | A61M 60/148 600/16 |
| 2016/0175503 | A1 * | 6/2016 | Smith | A61M 60/422 600/16 |
| 2016/0369814 | A1 * | 12/2016 | Schibli | A61M 60/205 |
| 2020/0330666 | A1 * | 10/2020 | Siess | A61M 60/419 |
| 2021/0001027 | A1 * | 1/2021 | Kirchhoff | A61M 60/135 |

FOREIGN PATENT DOCUMENTS

| | | |
|---|---|---|
| JP | 2010521261 A | 6/2010 |
| JP | 2015508678 A | 3/2015 |
| KR | 20140128434 A | 11/2014 |
| WO | 9844619 A1 | 10/1998 |
| WO | 2013120957 A1 | 8/2013 |

OTHER PUBLICATIONS

European Search Report for corresponding EP Application No. 18163761.2 dated Aug. 18, 2020 (8 pages).

International Search Report and Written Opinion for corresponding International Application No. PCT/EP2019/057011 dated Jun. 11, 2019 (9 pages).

Office Action from corresponding Indian Application No. 202037044994 dated May 30, 2022 (7 pages).

Office Action from corresponding Chinese Patent Application No. 201980022009.3 dated Feb. 18, 2023 (23 pp.).

Office Action from corresponding Japanese Patent Application No. 2020-551386 dated Feb. 21, 2023 (11 pp.).

Office Action from corresponding Israeli Patent Application No. 276900 dated Nov. 2, 2023 (4 pp.).

Office Action dated Jan. 11, 2024 for Korean patent application No. 10-2020-7030501 (14 pp.).

* cited by examiner

INTRAVASCULAR BLOOD PUMP WITH CERAMIC INNER SLEEVE

CROSS-REFERENCE TO RELATED APPLICATIONS

The present application is a national phase entry under 35 U.S.C. § 371 of International Application No. PCT/EP2019/057011, filed Mar. 20, 2019, published as International Publication No. WO 2019/180104 A1, which claims priority from European Patent Application No. 18163761.2, filed Mar. 23, 2018, all of which are incorporated herein by reference.

FIELD OF THE INVENTION

This invention relates to an intravascular blood pump for percutaneous insertion into a patient's blood vessel, in particular to be advanced into the patient's heart, and a respective method of manufacturing the intravascular blood pump.

BACKGROUND OF THE INVENTION

An intravascular blood pump designed to be inserted percutaneously into a patient's blood vessel, such as a femoral or axillary artery or vein, may be advanced into the patient's heart to act as a left ventricular assist device or right ventricular assist device. The blood pump may, thus, be referred to also an intracardiac blood pump. An intravascular blood pump typically comprises a catheter and a pumping device attached to a distal end of the catheter. The catheter may contain supply lines, such as an electric line and a purge line. Throughout this disclosure, the term "distal" will refer to directions away from a user and towards the heart, whereas the term "proximal" will refer to directions towards a user.

The pumping device may comprise an electric motor and an impeller coupled to a rotor of the electric motor for rotation of the impeller about an axis of rotation. During operation of the blood pump, the impeller conveys blood from a blood flow inlet to a blood flow outlet of the blood pump, for instance through a flow cannula. The pump rate depends on the size of the pumping device. In particular, the efficiency of the electric motor included in the pumping device is highly dependent on the limited space. However, it is desirable to reduce the size of the pumping device, in particular its diameter, because of anatomical limitations for insertion into a blood vessel.

In known intravascular blood pumps having a micro motor for driving the impeller of the blood pump, e.g. the blood pump disclosed in WO 98/44619 A1, the stator or at least stator parts of the electric motor are encapsulated in a casting compound, such as a polymer material, e.g. epoxy. According to a method of manufacturing the micro motor disclosed in WO 98/44619 A1, the stator parts of the motor are placed on a mandrel, which is then inserted into a mold cavity. A casting compound is injected into the mold cavity to encapsulate the stator parts and to form a housing of the pumping device.

An interior surface of the molded housing encloses a cavity in which the rotor of the electric motor is disposed, typically a magnet. The rotor will typically be in contact with a purge fluid, such as a glucose solution, which is supplied to the cavity by means of a purge line. In order to avoid corrosion of the stator parts, in particular a coil winding, which is typically provided and configured for generating a magnetic field, such as a rotating magnetic field, to cause rotation of the rotor, the casting compound forms a barrier for the purge fluid. However, since the coil winding is placed on the mandrel during injection-molding, there may be exposed spots of the coil winding on the interior surface of the housing, which defines the cavity. The coil winding also may have relatively large manufacturing tolerances, which cannot be compensated during injection molding.

SUMMARY OF THE INVENTION

It is therefore an object of the present invention to provide an intravascular blood pump, which provides improved sealing of electric parts of the blood pump against a purge fluid, while not increasing the diameter of the blood pump, and to provide a respective method of manufacturing such intravascular blood pump.

This object is achieved according to the present invention by an intravascular blood pump and a method of manufacturing the blood pump having the features of the independent claims. Preferred embodiments and further developments of the invention are specified in the claims dependent thereon.

According to an aspect of the invention, an intravascular blood pump for percutaneous insertion into a patient's blood vessel is provided. The blood pump comprises a pumping device including an impeller and an electric motor having a stator and a rotor for driving the impeller. The rotor is disposed inside a cavity in the pumping device and rotatable about an axis of rotation and coupled to the impeller so as to be able to cause rotation of the impeller. The cavity is formed by an inner sleeve made of a ceramic material, such as zirconia, or more preferably alumina toughened zirconia (ATZ). In particular the coil winding, which may be part of the stator as explained above, is preferably arranged on the inner sleeve.

By providing an inner sleeve made of a ceramic material a fluid tight enclosure of the cavity, in which the rotor is disposed, can be created. The ceramic material is diffusion resistant against the purge fluid. Thus, effective corrosion protection of the stator, in particular electric stator parts like the coil winding, can be achieved. Since the ceramic sleeve rather than the inner surface of the casting compound forms the cavity for the rotor, corrosion protection does not depend on the injection molding process, but the ceramic material of the inner sleeve forms a secure barrier against the purge fluid.

Apart from the sealing properties of the ceramic material, the ceramic inner sleeve can be manufactured with very small manufacturing tolerances. Thus, e.g. by placing the coil winding on the ceramic sleeve before injection molding, the dimensions of the coil winding, in particular the inner diameter and, thus, the outer diameter, can be defined and adjusted very precisely. The ceramic sleeve is substantially rigid and good to handle and may improve handling of the coil winding once the coil winding is placed on the sleeve. The ceramic material allows for a very small wall thickness of the inner sleeve, which is important for not increasing the overall diameter of the pumping device and for maintaining a small air gap between the stationary coil and the rotating magnet in order to ensure a high motor efficiency and low core temperature. In addition, the inner sleeve may be manufactured with a surface finish, in particular on the sleeve's inner surface, that even blood may be pumped through the air gap, i.e. the space between the inner sleeve and the rotor, without causing high blood damage or clotting. This may be relevant for a purge free pump.

In one embodiment, an end piece made of a ceramic material, preferably the same ceramic material the inner sleeve is made of, may be provided and attached to an axial end of the inner sleeve in a fluid tight manner to enclose the cavity. The ceramic end piece may be attached to the inner sleeve e.g. by an adhesive or may be integrally formed with the inner sleeve. Preferably, the end piece includes a bearing, such as a journal bearing, rotatably supporting the rotor. For instance, the rotor or a shaft carrying the rotor can be inserted into an aperture in the end piece to form a journal bearing.

The cavity is preferably in fluid communication with a purge line of the blood pump configured to supply a purge fluid into the cavity. In particular, the purge line may be connected to the aforementioned end piece. More specifically, the purge line may be connected to the end piece such that purge fluid is directly supplied to the bearing formed by the end piece, and through the bearing into the cavity. For instance, the end piece may include a central aperture and a central hollow post in alignment with the aperture, wherein the purge line may be connected to the hollow post.

The stator, specifically the coil winding and other electrical parts subject to corrosion, are preferably sealed against the cavity in a fluid tight manner by the inner sleeve. As explained above, the ceramic material effectively prevents diffusion of the purge fluid such that the stator parts are protected.

In one embodiment, electrical connections of the stator, preferably the coil winding, may be formed at least partially on the inner sleeve, preferably on the end piece. The ceramic inner sleeve and possibly the ceramic end piece are suitable for carrying electrical connections because the ceramic material withstands high temperatures during soldering the electrical connections, e.g. copper pads connecting to wires (usually copper wires) of the coil winding. In particular, if a large number and complex arrangement of the terminals of the coil winding is necessary, it may be advantageous to arrange the electrical connections, in particular the copper pads, on the ceramic inner sleeve and/or the ceramic end piece. The copper pads may be formed by copper coating the ceramic sleeve and/or the ceramic end piece at desired locations.

In order to be able to control the coil winding for generating a magnetic field, in particular a rotating magnetic field, a relatively large number of electrical connections of the coil winding is needed. For instance, in order to control the coil winding in multiple phases, e.g. three phases, to create a rotating magnetic field, six electrical connections are necessary in a two-layer arrangement of the wires of the coil winding. More specifically, the coil winding may be divided in multiple angular sections, e.g. three sections of 120 degrees each, which are sequentially controllable to cause rotation of the rotor, which may be a permanent magnet. A more powerful four-layer arrangement would then need twelve electrical connections.

In order to achieve an arrangement of e.g. three controllable sections of the coil winding, the coil wire may be looped out and cut to create two terminals during winding the wire at 120 degrees and 240 degrees to close one section and begin a subsequent section. Thus, in a two-layer coil arrangement, this results in six terminals, namely one at the beginning (at 0 degrees), two at 120 degrees, two at 240 degrees, and one at the end (at 360 degrees, which is identical to the 0-degree position). It will be appreciated that only two sections of 180 degree each, or more than three sections may be provided if desired, as long as a dynamic magnetic field for causing rotation of the rotor can be created.

A typical winding pattern, in which the wire starts at 0 degrees at one longitudinal end of the coil winding, is guided towards the opposing longitudinal end at a 180-degree position and returns to the starting point to finish one cycle, results in an even number of winding layers. In order to keep the outer diameter of the coil winding as small as possible, a subsequent layer may be offset by half of the diameter of the coil wire perpendicular to a longitudinal direction of the coil wire so as to nest the subsequent layer between the wires of the underlying layer.

Providing a precise arrangement of the layers of the coil winding, in particular without crossings or gaps, is important for the efficiency of the electric motor on the one hand, and for keeping the outer diameter within narrow manufacturing tolerances on the other hand. In particular, the wire sections of the coil winding should be exactly placed side by side along their length without imperfections in form of crossovers. Placing the wires exactly side by side may further improve structural stability of the coil winding because an exact arrangement allows for properly securing the wire sections to adjacent wire sections by means of their insulting coating, which may include a thermosetting varnish, such as baking lacquer, as the outermost layer. Providing a ceramic inner sleeve as a support for the coil winding may help to provide an improved and precise arrangement of the wires of the coil winding in particular with respect to the aforementioned aspects.

As outlined above, the inner sleeve may have a small wall thickness. More specifically, the inner sleeve may have a wall thickness of about 20 µm to about 100 µm, preferably about 40 µm to about 60 µm, more preferably about 50 µm. The inner sleeve may have a tubular shape. Preferably, the inner sleeve is substantially cylindrical. An inner diameter of the inner sleeve is preferably slightly larger than an outer diameter of the rotor to form a small gap e.g. of about 50 µm. A small gap is preferred with respect to optimizing the magnetic flux to optimize efficiency of the electric motor as mentioned above. At this point it will be appreciated that another advantage of the ceramic material is that it does not affect the magnetic flux of the electric motor. The inner sleeve may have a length of about 5 mm to about 20 mm, preferably about 8 mm to about 15 mm.

The intravascular blood pump may further comprise an outer sleeve which may form at least a portion of an outer surface of the pumping device. At least a portion of the stator may then be disposed in an interspace between the outer sleeve and the inner sleeve. The outer sleeve may comprise a magnetically conductive material, such as a metal or metal alloy, to form a yoke (back iron) of the electric motor. The stator, or at least stator parts, preferably at least the coil winding, may be fixed outside the inner sleeve, in particular in the interspace between the inner sleeve and outer sleeve, by means of a casting compound, such as a polymer material like epoxy.

In a method of manufacturing an intravascular blood pump, in particular an intravascular blood pump as described above, an inner sleeve made of a ceramic material to form the cavity for receiving the rotor is provided and the coil winding is arranged on the inner sleeve. The ceramic sleeve thereby forms a support for the coil winding, which can be easily handled as described above. Further, as also explained in the aforementioned, the ceramic inner sleeve has very small manufacturing tolerances, which allows for very precise calibration of the coil winding. The coil winding may be pre-wound and then placed on the ceramic sleeve, whereby the coil winding can be adjusted to the dimensions of the ceramic sleeve. Alternatively, the coil winding may be wound directly onto the ceramic sleeve. In any case, the coil winding is centered correctly by the ceramic sleeve.

As mentioned above, the ceramic inner sleeve may be connected to a ceramic end piece, which may include a bearing. Thus, the method may further comprise attaching an end piece made of a ceramic material to an axial end of the inner sleeve in a fluid tight manner to enclose the cavity. The end piece may be attached to the inner sleeve by gluing or other adhesive methods. This may be carried out before placing the coil winding on the inner sleeve, and possibly before injection-molding a casting compound around the inner sleeve.

The method may further comprise injection-molding a casting compound around the inner sleeve to encapsulate at least the coil winding arranged on the inner sleeve. If the pumping device comprises an outer sleeve as mentioned above, the injection-molding may be particularly carried out by injecting the casting compound into the outer sleeve, more specifically an interspace formed between the inner sleeve and the outer sleeve. However, it will be appreciated that the ceramic inner sleeve may be provided independently from an outer sleeve, and the stator parts may be encapsulated by any other injection-molding technique, e.g. by injecting a casting compound into a mold as described e.g. in WO 98/44619 A1.

In a method of manufacturing the blood pump using an outer sleeve as a mold during the injection-molding process, the ceramic inner sleeve and further stator components, such as a coil winding, may be placed on a molding base, which may be formed as a mandrel. The outer sleeve, which may be considered as the outermost of the stator components, may then be placed on the molding base, and thereby over the inner sleeve and the other stator components, to thereby form at least a portion of an outer surface of the blood pump and to form an interspace between the inner sleeve and the outer sleeve in which the stator components are disposed. A casting compound, such as a polymer material, in particular a resin like epoxy, may then injected into said interspace via the molding base to fix the stator components inside the outer sleeve. The molding base may be a disposable piece, made of plastic, e.g. by injection-molding.

This may be particularly advantageous if the outer sleeve comprises a magnetically conductive material to form a yoke (back iron) of the electric motor. In particular, the outer sleeve may comprise or may be made of a metal or metal alloy, such as a ferritic alloy, e.g. a FeCrAl alloy. The outer surface may be covered with a respective oxide. It will be appreciated that the outer sleeve may comprise any suitable biocompatible magnetically conductive material. A metal material has the further advantage heat dissipation is increased compared to a plastic material.

BRIEF DESCRIPTION OF THE DRAWINGS

The foregoing summary, as well as the following detailed description of preferred embodiments, will be better understood when read in conjunction with the appended drawings. For the purpose of illustrating the present disclosure, reference is made to the drawings. The scope of the disclosure is not limited, however, to the specific embodiments disclosed in the drawings. In the drawings.

DETAILED DESCRIPTION

Figure 1:
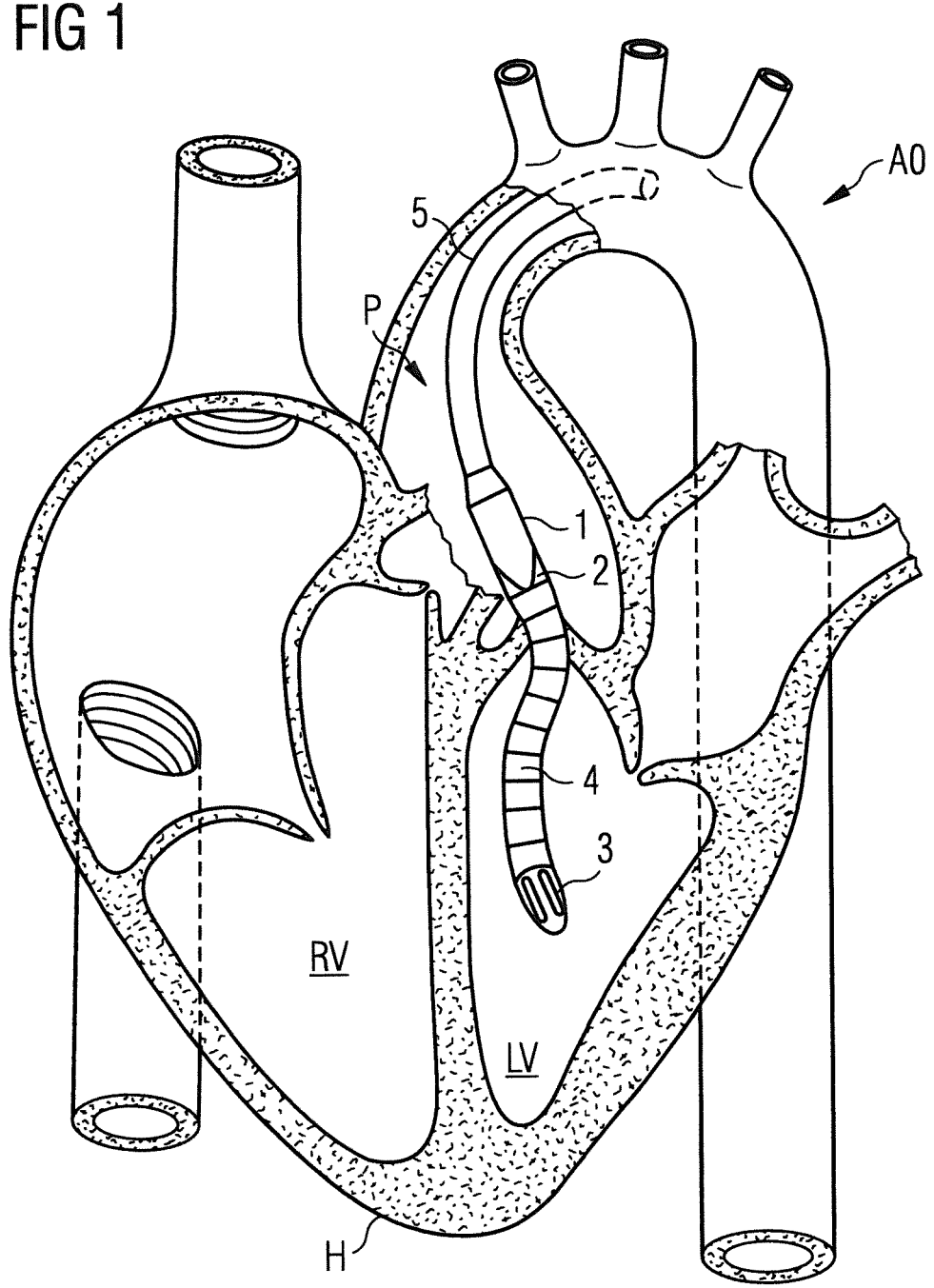
FIG. 1 schematically shows an intravascular blood pump inserted into a patient's heart.

In FIG. 1 is illustrated an intravascular blood pump P inserted into a patient's heart H. More specifically, the blood pump P comprises a pumping device 1 attached to a catheter 5 by means of which the pumping device 1 is inserted into the left ventricle LV of the patient's heart H to pump blood from the left ventricle LV into the aorta AO. The shown application is only an exemplary application, and the blood pump P of the present invention is not limited to this application. For instance, reverse applications for the right ventricle RV may be envisioned. The blood pump P is percutaneously inserted e.g. via a femoral access or an axillary access and is advanced through the aorta AO into the heart H. The blood pump P is placed such that a blood flow outlet 2 is disposed outside the patient's heart H in the aorta AO, while a blood flow inlet 3 which is in flow communication with a flow cannula 4 is disposed inside the left ventricle LV. An impeller is provided in the pumping device 1 to cause the blood flow from the blood flow inlet 3 to the blood flow outlet 2, and rotation of the impeller is caused by an electric motor disposed in the pumping device 1 as will be explained in more detail below.

Figure 2:
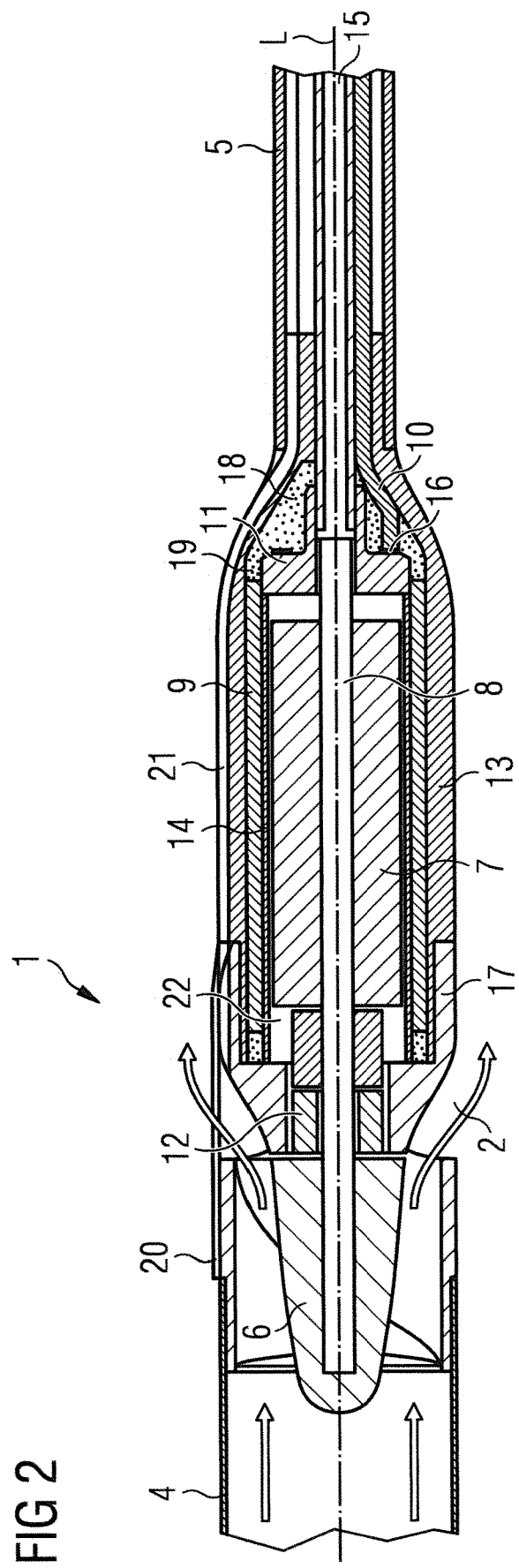
FIG. 2 shows a cross-section through the intravascular blood pump.

FIG. 2 shows a cross-sectional view through the pumping device 1 along a central longitudinal axis L, which is coincident with an axis of rotation of the rotor 7 and the impeller 6. More specifically, the rotor 7 and the impeller 6 are arranged on a common shaft 8 which extends along the axis of rotation. The rotor 7 of the electric motor is formed as a permanent magnet and is disposed inside a cavity 22 of the pump casing. In order to cause rotation of the rotor 7, a coil winding 9 as part of a stator of the electric motor surrounds the rotor 7 and is controllable so as to cause rotation of the rotor 7. The impeller 6 is coupled to the rotor 7 via the shaft 8 such that rotation of the rotor 7 causes rotation of the impeller 6 to thereby draw blood into the blood flow inlet 3 and through the flow cannula 4 out of the blood flow outlet 2 as indicated by the arrows in FIG. 2.

The shaft 8 is rotatably supported by a distal bearing 12 and a proximal bearing 11, both of which may be formed as a journal bearing as shown in FIG. 2. The bearings 11, 12 and the shaft 8 may be formed of a ceramic material. However, other types of bearings, such as ball bearings, may be used for rotatably supporting the shaft 8. The bearings may be axial bearings or radial bearings or combined axial and radial bearings. A purge fluid is supplied through the bearings 11, 12 and the cavity 22 in which the rotor 8 is located by means of a purge line 15. The purge line 15 extends through the catheter 5 and is connected to the proximal bearing 11 in a fluid tight manner. In this way, the purge fluid does not come into contact with electrical components of the pumping device 1 but only flows through the proximal bearing 11, into the cavity 22 and through the distal bearing 12.

In order to provide a secure barrier to protect the electrical components, in particular the coil winding 9, from corrosion and short circuits caused by the purge fluid, the cavity 22 for the rotor 7 may be formed by an inner sleeve 14, which is made of a ceramic material. The ceramic inner sleeve 14 is attached to the proximal bearing 11 in a fluid tight manner and is resistant against diffusion of the purge fluid. The ceramic inner sleeve 14 is so well defined also with a smooth inner surface that in another configuration of the blood pump some blood can be allowed to enter the pump instead of the purge fluid without clotting or blood destruction. Further corrosion protection is established by a casting compound 18, which fixes the stator components of the pumping device 1 and fills an interspace 19 between the inner sleeve 14 and an outer sleeve 13. In particular, the coil winding 9 is encapsulated in the casting compound 18. The casting compound 18 also provides additional fixation for the electrical connections 16 (i.e. the PCB) with the motor cable 10 as well as the purge line 15. The casting compound 18 may be a polymer material like a resin, preferably a two-component epoxy, and more preferably a two-component epoxy with a heat conducting and electrically insulating filler.

The outer sleeve 13 defines the outer surface and the outer dimensions of the pumping device 1. Thus, the casing of the pumping device 1 is formed by the outer sleeve 13, which encloses the aforementioned components, in particular the stator components fixed by the casting compound 18. It will be appreciated that the outer sleeve 13 also forms a stator component, which is magnetically active. The outer sleeve 13 is made of a biocompatible magnetically conductive material, such as a suitable metal alloy, and serves as a yoke for the magnetic flux of the electric motor. The metal outer sleeve 13 also allows for good dissipation of heat caused by operation of the electric motor. The outer surface of the outer sleeve 13 may include a groove 21 for receiving a line with a sensor 20. A hub 17 is attached to the distal end of the outer sleeve 13 and forms an attachment area for the flow cannula 4. The hub 17 is preferably made of the same material as the outer sleeve 13 and accommodates the distal bearing 12 and the impeller 6. The blood flow outlet 2 is formed in the hub 17, such that heat transfer away from the distal bearing 12 is possible.

The outer sleeve 13 may have a length of about 7 mm to about 30 mm, preferably about 10 mm to about 20 mm, more preferably about 10 mm to about 15 mm. The outer sleeve 13 may have an outer dimension of 18F (French) or smaller (outer diameter of 6 mm or smaller). Despite the small dimensions, a pump rate of up to 5.5 liters per minute may be achieved.

Figure 3:
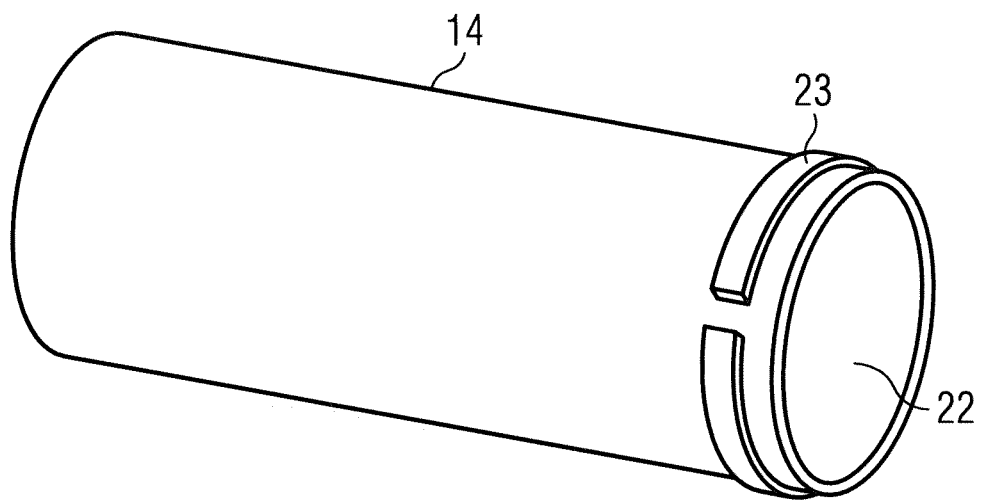
FIG. 3 shows a perspective view of the ceramic inner sleeve.

FIG. 3 illustrates the ceramic inner sleeve 14 included in the aforementioned intravascular blood pump P enclosing the cavity 22 for the rotor 7. The sleeve 14 has a cylindrical shape and a wall thickness of about 20 μm to about 100 μm, preferably about 50 μm. The ceramic material may be alumina toughened zirconia (ATZ). Electrical connections for the coil winding 9, in particular copper pads 23 for soldering electrical connections, may be provided directly on the ceramic sleeve 14, e.g. by copper coating the respective locations on the sleeve 14. The ceramic material withstands high temperatures during soldering and is therefore suitable to form a support for the copper pads 23, in other words the PCB. The sleeve 14 may carry three copper pads 23 circumferentially and regularly disposed on the surface of the sleeve 14.

Figure 4:
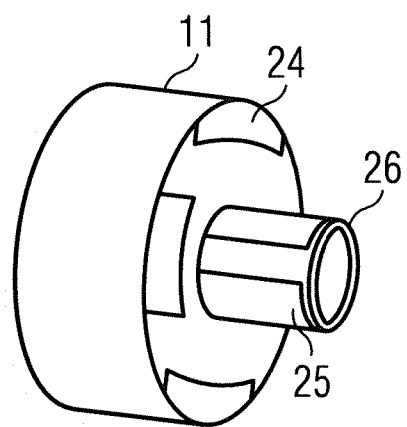
FIG. 4 shows a perspective view of the ceramic proximal bearing.

In order to be able to sequentially control the coil winding 9 for creating a rotating magnetic field, there are at least six terminals of the coil winding 9 if the coil winding is applied in a two-layer arrangement. In a four-layer arrangement of the coil winding, twelve terminals have to be connected. Thus, additional electrical connections 24, 25 may be arranged on the ceramic end piece 11, which includes the proximal bearing, as shown in FIG. 4. The end piece 11 may be made of the same ceramic material as the inner sleeve 14 and may be attached to the inner sleeve 14 by adhesive. The central aperture of the end piece 11 is sized and shaped to rotatably receive the shaft 8 of the rotor 7. A central hollow stem 26 protruding from the end piece 11 in alignment with the central aperture is provided as an attachment area for the purge line 15. In this manner, the purge fluid is fed directly to the bearing and further into the inside of the inner sleeve 14.

In a method of manufacturing the intravascular blood pump, the end piece 11 may be attached to the inner sleeve 14 to form a fluid tight enclosure for the rotor 7. The coil winding 9, which may be pre-wound, can be placed on the inner sleeve 14, which allows for precise adjustment of the dimensions of the coil winding 9. Thus, the ceramic inner sleeve 14 not only provides a tight barrier for the purge fluid and an electrical insulation but also helps to improve the efficiency of the electric motor by optimizing the arrangement of the coil winding 9. The terminals of the coil winding 9 are soldered to the copper pads 23, 24, 25 and the coil winding 9 mounted on the inner sleeve 14 is further processed, e.g. encapsulated in a casting compound 18 in an injection-molding process.

In another method, the coil winding 9 may be wound directly on the inner sleeve 14 and interconnections of the coil winding 9 and the copper pads 23, and if applicable the copper pads 24, 25, may be done automatically during the winding process. Thus, a secondary soldering step and specific sorting of the terminals wires of the coil winding 9 (e.g. by length or color of the terminal wires) can be avoided.

The invention claimed is:

1. An intravascular blood pump for percutaneous insertion into a patient's blood vessel, comprising a pumping device including an impeller and an electric motor for driving the impeller, the electric motor including a stator and a rotor, the stator including coil winding layers comprising wires arranged such that the wires of the coil winding are placed exactly side by side along their length without crossovers and the rotor disposed inside a cavity in the pumping device and rotatable about an axis of rotation and coupled via a shaft to the impeller so as to be able to cause rotation of the impeller, wherein the cavity is formed by an inner sleeve made of a ceramic material and the coil winding layers are formed on and over the ceramic inner sleeve.

2. The blood pump according to claim 1, wherein the stator comprises a coil winding arranged on the inner sleeve and configured for generating a magnetic field to cause rotation of the rotor.

3. The blood pump according to claim 1, further comprising an end piece made of a ceramic material and attached to an axial end of the inner sleeve in a fluid tight manner to enclose the cavity.

4. The blood pump according to claim 3, wherein the end piece includes a bearing rotatably supporting the shaft.

5. The blood pump according to claim 1, wherein the cavity is in fluid communication with a purge line of the blood pump configured to supply a purge fluid into the cavity.

6. The blood pump according to claim 1, wherein the stator is sealed against the cavity in a fluid tight manner by the inner sleeve.

7. The blood pump according to claim 1, wherein electrical connections of the stator are formed at least partially on the inner sleeve.

8. The blood pump according to claim 1, wherein the inner sleeve has a wall thickness of between 40 μm and 60 μm.

9. The blood pump according to claim 1, wherein the inner sleeve is substantially cylindrical.

10. The blood pump according to claim 1, wherein at least a portion of the stator is fixed outside the inner sleeve by means of a casting compound.

11. The blood pump according to claim 1, further comprising an outer sleeve which forms at least a portion of an outer surface of the pumping device, wherein at least a portion of the stator is disposed in an interspace between the outer sleeve and the inner sleeve.

12. The blood pump according to claim 11, wherein the outer sleeve comprises a magnetically conductive material to form a yoke of the electric motor.

13. A method of manufacturing an intravascular blood pump, the blood pump comprising a pumping device including an impeller and an electric motor for driving the impeller, the electric motor including a stator and a rotor, the rotor rotatable about an axis of rotation and coupled via a shaft to the impeller so as to be able to cause rotation of the impeller, the method comprising the steps of:

providing an inner sleeve made of a ceramic material to form a cavity for receiving the rotor; and arranging a coil winding on and over the inner sleeve for generating a magnetic field to cause rotation of the rotor wherein the coil winding comprises wires that are arranged exactly side by side along their length without crossovers.

14. The method according to claim 13, further comprising the step of attaching an end piece made of a ceramic material to an axial end of the inner sleeve in a fluid tight manner to enclose the cavity, wherein the end piece includes a bearing rotatably supporting the rotor.

15. The method according to claim 13, further comprising the step of injection-molding a casting compound around the inner sleeve to encapsulate at least the coil winding arranged on the inner sleeve.

16. The blood pump according to claim 4, wherein the bearing is a journal bearing.

17. The method according to claim 14, wherein the bearing is a journal bearing.

18. The blood pump according to claim 12, wherein the outer sleeve comprises a metal or metal alloy.

19. The blood pump according to claim 10, wherein the casting compound comprises a polymer material.

20. The blood pump according to claim 10, wherein the casting compound comprises a resin or an epoxy.

* * * * *